United States Patent [19]
Morris

[11] Patent Number: 4,576,758
[45] Date of Patent: Mar. 18, 1986

[54] ANTI-INFLAMMATORY LIPOXIN B ANALOGS

[75] Inventor: Joel Morris, Kalamazoo, Mich.

[73] Assignee: The Upjohn Company, Kalamazoo, Mich.

[21] Appl. No.: 616,456

[22] Filed: Jun. 1, 1984

[51] Int. Cl.$^4$ ............................................... C09F 5/00
[52] U.S. Cl. .............................. 260/405.5; 560/103; 556/482; 260/413
[58] Field of Search ................ 260/410, 410 R, 410.5, 260/410.6, 410.9, 413, 405.5, 413 L, 413 K

[56] References Cited

U.S. PATENT DOCUMENTS

| | | | |
|---|---|---|---|
| 2,934,570 | 4/1960 | Goldberg et al. | 260/413 |
| 3,972,907 | 8/1976 | Baran et al. | 260/410.9 |
| 4,112,224 | 9/1978 | Bundy | 260/244.4 |
| 4,264,517 | 4/1981 | Liang | 260/410.5 |

OTHER PUBLICATIONS

Jubiz, W., et al., *Biochem. Biophys. Res. Commun.* 99:976-986 (1981).
Radmark, O., et al., In: *Advances in Prostaglandin, Thromboxane & Leukotriene Research*, vol. 11, pp. 61-70, Raven Press, NY (1982).
Maas, R. L., et al., *Proc. Natl. Acad. Sci.* 78:5523-5527 (1981).
Lagarde, M., et al., *Biochem. Biophys. Res. Commun.* 99:1398-1402 (1981).
Vanderhoek, J. Y., et al., *J. Biol. Chem.* 255:5996-5998 and 255:10064-10066 (1980).
Samuelsson, B., *Science* 220:568-565 (1983).
Weissman, G., et al., *N. Engl. J. Med.* 303:27-34 (1980).
Serhan, C. N., *J. Immunol.* 125:2020-2024 (1980).
Lewis, R. A., et al., *J. Exp. Med.* 154:1243-1248 (1981).
Serhan, C. N., et al., *Biochem. Biophys. Res. Commun.* 107:1006-1012 (1982).
Lundgerg, U., et al., *FEBS Lett.* 126:127-132 (1981).
Maas, R. L. et al., *Proc. Natl. Acad. Sci.* 80:2884-2888 (1983).
Sok, D-E, et al., *Biochem. Biophys. Res. Commun.* 104:1363-1370 (1981).
Sok, D-E, et al., *Biochem. Biophys. Res. Commun.* 110:273-279 (1983).
Turk, J., et al., *J. Biol. Chem.* 257:7068-7076 (1982).
Turk, J. et al., *Biochim. Biophys. Acta* 750:78-90 (1983).
Turk, J. et al., *Advances in Prostaglandin, Thromboxane & Leukotriene Research*, vol. 11, pp. 123-132, Raven Press, N.Y. (1983).
Maas, R. L., et al., *J. Biol. Chem.* 257:7056-7067 (1982).
Maas, R. L., et al., *Leukotrienes and Other Lypoxygenase Products*, Raven Press, N.Y. (1982), pp. 29-44.
Serhan, C. N., *Biochem. Biophys. Res. Commun.* 118:943-949 (1984).

Primary Examiner—James H. Reamer
Attorney, Agent, or Firm—Robert A. Armitage

[57] ABSTRACT

The present invention relates to analogs of lipoxin B (LX-B) and discloses the anti-inflammatory uses for these analogs. Particularly, the present invention relates to analogs of 5D,14,15-trihydroxy-6,8,10,12-eicosatetraenoic acid, including certain 5-epi-, 8,9-didehydro-, 6-iso, 6,7-dihydro-7α-hydroxy, and 6,7-dihydro-7β-hydroxy derivatives.

20 Claims, No Drawings

4,576,758

ANTI-INFLAMMATORY LIPOXIN B ANALOGS

BACKGROUND OF THE INVENTION

The present invention relates to novel chemical compounds, pharmacological uses and compositions therefor. Particularly, the present novel invention relates to analogs of lipoxin B (LX-B) or 5D,14,15-trihydroxy-6,8,10,12-eicosatetraenoic acid and uses therefor. Also, the present invention relates to novel methods and intermediates for the synthesis of LX-B compounds.

Arachidonic acid plays a central role in a complex system of biological controls wherein oxygenated derivatives of a arachidonic acid, such as prostaglandins, thromboxanes, and leukotrienes are mediators. Each of these classes of compounds are metabolites of arachidonic acid and include, for example, $PGF_2\alpha$, prostacyclin or $PGI_2$, and thromboxane $A_2$. Each of these substances are formed from arachidonic acid through prostaglandin endoperoxide precursors, i.e., $PGG_2$ and $PGH_2$, through the action of a cyclooxygenase enzyme on the arachidonic acid substrate.

In contrast to the cyclopentane-containing prostaglandins and thromboxanes, the leukotrienes are acyclic arachidonic acid metabolites which are formed by transformation of arachidonic acid into an unstable epoxide intermediate, leukotriene $A_4$, which can be converted enzymatically by hydration to leukotriene $B_4$ and by addition of glutathione to leukotriene $C_4$. Leukotriene $C_4$ is metabolized to leukotriene $D_4$ and leukotriene $E_4$ by successive elimination of a gamma-glutamyl residue and glycine.

The aforementioned leukotrienes are known in the art as mediators of immediate hypersensitivity reactions and inflammation. In particular, the slow-reacting substance of anaphylaxis (SRS-A) consists of leukotrienes $C_4$, $D_4$ and $E_4$. The cysteinyl-containing leukotrienes are also potent bronchoconstrictors, increase vascular permeability in post-capillary venules, and stimulate mucus secretion. Leukotriene $B_4$ causes adhesion and chemotactic movement of leukocytes and stimulates aggregation, enzyme release, and the generation of superoxide in neutrophils. Leukotriene $C_4$, $D_4$ and $E_4$, which are released from the lung tissue of asthmatic subjects exposed to specific allergens, play a pathophysiological role in immediate hypersensitivity reactions. As such, these leukotrienes, as well as leukotriene $B_4$, have marked pro-inflammatory effects.

The first series of leukotrienes were discovered from products, e.g., 5-hydroperoxyeicosatetraenoic acid (5-HPETE), derived enzymatically from arachidonic acid through the action of a 5-lypoxygenase enzyme. For discussion of the various leukotriene metabolites of 5-HPETE, their formation and biological effects, see Bengt Samuelsson, "Leukotrienes: Mediators of immediate hypersensitivity reactions in inflammation," *Science* 220:568–575 (1983).

These originally discovered leukotrienes were all characterized by the initial introduction of an oxygen atom at the C-5 position. However, other enzymatic pathways were subsequently identified wherein lipoxygenase enzymes catalyze the introduction of oxygen atom at other positions besides C-5. Particularly known are leukotrienes formed with initial oxygenation at either C-12 or C-15 through 12- or 15-lipoxygenases. For example, a 15-lipoxygenase converts arachidonic acid to 15-hydroperoxy-eicosatetraenoic acid (15-HPETE). This compound is then further metabolized to 14,15-dihydroxy-5,8,10,12-eicosatetraenoic acid (14,15-diHETE) as well as 8,15-dihydroxy-5-cis-9,11,13-trans-eicosatetraenoic acids.

The present disclosure provides analogs of one series of a new family of oxygenated derivatives of arachidonic acid which arise through interactions of multiple distinct lipoxygenase pathways and therefore are given the name "lipoxins", or LX compounds. These novel lipoxins are, like the leukotrienes, oxygenated derivatives of arachidonic acid. They contain, however, a trihydroxy-tetraene structure instead of the characteristic triene structure of the leukotrienes.

Neutrophils are leukocytes which mediate inflammatory processes in mammals. They aggregate, degranulate, generate active oxygen species, and release oxidation products of arachidonate when exposed to appropriate stimuli (See G. Weissman et al. (1980) *N. Engl. J. Med.* 303:27–34 and C. W. Serhan et al. (1980) *J. Immunol.* 125:2020–2024). Upon activation, human neutrophils release arachidonic acid from membrane phospholipids which may be oxygenated by either cyclooxygenase (prostaglandins, prostacyclin, or thromboxane) or lipoxygenase (leukotriene) pathways. For example, activation of the 5-lipoxygenase pathway leads to the formation of $LTB_4$ and its isomers, as indicated above. The fact that $LTB_4$ is a potent chemo-attractant and is the agent which stimulates secretion in human neutrophils (See R. A. Lewis et al. (1981) *J. Exp. Med.* 154:1243–1248 and C. N. Serhan et al. (1982) *Biochem. Biophys. Res. Commun.* 107:1006–1012) indicates that activation of the 5-lipoxygenase pathway plays a key role in the inflammatory response in mammals.

In addition to pro-inflammatory effects associated with the 5-lipoxygenase pathway, human leukocytes are also capable of oxygenating arachidonate by means of the 15-lipoxygenase pathway as indicated above. See U. Lundberg et al. (1981) *FEBS Lett.* 126:127–132; W. Jubiz et al. (1981) *Biochem. Biophys. Res. Commun.* 99:976–986; and O. Radmark et al. (1982) In: *Advances in Prostaglandin, Thromboxane and Leukotriene Research* (eds. B. Samuelsson, P. Ramwell and R. Paoletti), vol. 11, Raven Press, NY, pp. 61–70. Initial oxygenation at C-15 leads to the formation of 15-hydroperoxyeicosatetraenoic acid (15-HPETE) which may be further transformed to 14,15- or 8,15-hydroperoxyeicosatetraenoic acids, as indicated above. See U. Lundberg et al. (1981) *FEBS Lett.* 126:127–132; W. Jubiz et al. (1981) *Biochem. Biophys. Res. Commun.* 99:976–986; O. Radmark et al. (1982) In: *Advances in Prostaglandin, Thromboxane and Leukotriene Research* (eds. B. Samuelsson, P. Ramwell and R. Paoletti), vol. 11, Raven Press, NY, pp. 61–70; and R. L. Maas et al. (1981) *Proc. Natl. Acad. Sci.* 78:5523–5527. A biological role for the 15-lipoxygenase pathway and its metabolites has not heretofore been elucidated. Recent studies indicate that 15-HPETE inhibits the release of arachidonate from platelets (see M. Lagarde et al. (1981) *Biochem. Biophys. Res. Commun.* 99:1398–1402) and that 15-HETE, a metabolic product of 15-HPETE, inhibits not only the 12-lipoxygenase but also leukotriene biosynthesis (see J. Y. Vanderhoek et al. (1980) *J. Biol. Chem.* 255:5996–5998 and J. Y. Vanderhoek et al. (1980) *J. Biol. Chem.* 255:10064–10065).

INFORMATION DISCLOSURE

The existence of C-15 hydroxylated leukotriene-type compounds and a biochemical pathway by which arachidonic acid is converted to such compounds through a 15-lipoxygenase pathway is known. See Maas, R. L. et al., *Proceedings of the National Academy of Sciences, USA*, 80:2884–2888 (1983); Maas, R. L. et al., *Proceedings of the National Academy of Sciences, USA*, 78:5523–5527 (1981); Sok, D-E, et al., *Biochemical and Biophysical Research Communications*, 104:1363–1370 (1981); Sok, D-E, et al., *Biochemical and Biophysical Research Communications*, 110:273–279 (1983); Jubiz, W., et al., *Biochemical and Biophysical Research Communications*, 99:976–986 (1981); Turk, J., et al., *Journal of Biological Chemistry*, 257:7068–7076 (1982); Turk, J., et al., *Biochimica et Biophysica Acta*, 750:78–90 (1983); Turk, J., et al., "Conjugated triene metabolites of arachidonic acid derived from dioxygenation at carbon 15: Origin from eosinophil and mechanisms of biosynthesis," in: "Advances in Prostaglandin, Thromboxane and Leukotriene Research," Eds. B. Samuelsson, et al., Vol. 11, Raven Press, New York (1983); Maas, R. L., et al., *Journal of Biological Chemistry*, 257:7056–7067 (1982); Maas, R. L., et al., "Novel leukotrienes and lypoxygenase products from arachidonic acid" in: "Leukotrienes and Other Lypoxygenase Products," Eds. B. Samuelsson, et al., Raven Press, New York, (1982); and Radmark, O., et al., "New group of leukotrienes formed by initial oxygenation at C-15" In: "Leukotrienes and other lypoxygenase products," eds. B. Samuelsson, et al., Raven Press, New York, (1982).

Subsequent to the making of the invention thereof herein, the existence of lipoxin A, a trihydroxy-tetraene derived from arachidonic acid, was reported by Serhan, C. N., Hamberg, M., and Samuelsson, B., *Biochem. Biophys, Res. Commun.*, 118:943–949 (1984).

SUMMARY OF THE INVENTION

The present invention relates to the total chemical synthesis of lipoxin B and analogs thereof. In particular, the present invention specifically relates to:

a LX-B analog of formula XV wherein X is cis—CH=CH— or —C≡C—;

wherein Y is cis—CH=CH—, trans—CH=CH—, or —CH$_2$—CH(OH)—; and wherein R$_1$ is C$_1$–C$_{12}$ alkyl; C$_3$–C$_{10}$ cycloalkyl; C$_7$–C$_{12}$ aralkyl; phenyl optionally substituted by one, two, or three C$_1$–C$_3$ alkyl, C$_1$–C$_3$ alkoxy, chloro, fluoro, or trifluoromethyl with the proviso that not more than two such substituents are other than alkyl; hydrogen; or a pharmacologically acceptable cation;

with the overall proviso that Y is trans—CH=CH— and X is cis—CH=CH— only when the hydroxyl configuration at C-5 is alpha.

These analogs of lipoxin B specifically include compounds varying in unsaturation and functionalization. Specifically included are the following lipoxin B analogs:

5-epi-LX-B,
8,9-didehydro-LX-B,
5-epi-8,9-didehydro-LX-B,
6-iso-LX-B, 5-Epi-6-iso-LX-B,
8,9-didehydro-6-iso-LX-B,
5-epi-8,9-didehydro-6,7-dihydro-7α-hydroxy-LX-B,
6,7-dihydro-7α-hydroxy-LX-B,
5-epi-6,7-dihydro-7α-hydroxy-LX-B,
8,9-didehydro-6,7-dihydro-7α-hydroxy-LX-B,
5-epi-8,9-didehydro-6,7-dihydro-7α-hydroxy-LX-B,
6,7-dihydro-7β-hydroxy-LX-B,
5-epi-6,7-dihydro-7β-hydroxy-LX-B,
8,9-didehydro-6,7-dihydro-7β-hydroxy-LX-B,
5-epi-8,9-didehydro-6,7-dihydro-7β-hydroxy-LX-B,
5-epi-LX-B, methyl ester,
8,9-didehydro-LX-B, methyl ester,
5-epi-8,9-didehydro-LX-B, methyl ester, and
5-epi-LX-B, sodium salt.

The system of nomenclature employed herein for naming these lipoxins is wholly analogous to the nomenclature for other eicosanoids, i.e., prostaglandins, thromboxanes, prostacyclins and leukotrienes.

These lipoxin B analogs are synthesized by methods particularly described in the charts herein after. In general, the synthetic schemes employed in these charts utilize chemical methodologies and procedures generally known for the total chemical synthesis of other eicosanoids. Accordingly, all starting materials herein are known in the art or can be prepared by standard synthetic methods for synthesis of fatty acids.

The lipoxin B analogs in accordance with the present invention are useful for the same pharmacological purposes for which lipoxin B is useful.

Accordingly, the present invention further provides:
(a) a method for attenuating the activation of neutrophils in response to a stimulus which comprises:
    exposing the neutrophils to a concentration of an LX-B analog of formula XV effective to stimulate the activation of neutrophils being so exposed;
(b) a method for
    (1) preventing inflammation or an inflammatory response in a mammal susceptible to the development of an inflammation or an inflammatory response,
    (2) or treating a mammal suffering from an inflammation or inflammatory disease or condition,
    which comprises:
    administering to said mammal an amount of an LX-B analog of formula XV effective to prevent or treat said inflammation, an inflammatory response, or inflammatory disease or condition; and
(c) an anti-inflammatory pharmaceutical composition in a unit dosage form which comprises:
    an amount of an LX-B analog of formula XV effective to prevent or treat inflammation, an inflammatory response, or inflammatory disease or condition in a mammal to whom one or more unit doses of said composition are administered periodically in the course of a regimen of treatment.

The present invention provides a novel method for attenuating the activation of neutrophils in mediating inflammation. Specifically the present invention provides a method by which neutrophil activation and the generation of superoxide anions are inhibited utilizing LX-B analogs of formula XV. Accordingly, the novel LX-B analogs are useful for inducing anti-inflammatory responses and thus facilitate the study and understanding of inflammatory process and, accordingly are useful in the design and testing of anti-inflammatory properties of other pharmacologically active agents.

The present invention also provides a novel method for treating inflammation, an inflammatory response, or an inflammatory disease or condition by virtue of the capacity of the novel LX-B analogs for attenuating the activation of neutrophils in mediating inflammation. Specifically, the present invention provides a method by which neutrophil aggregation, the generation of superoxide anions by neutrophils, and the formation of pro-inflammatory leukotrienes by neutrophils through the 5-lipoxygenase pathway are inhibited by the LX-B analogs.

The present invention further provides novel pharmaceutical compositions useful in preventing or treating inflammation. The pharmacologically active agent in these pharmaceutical compositions is an LX-B analog of formula XV.

The method in accordance with the present invention for attentuating the activation of neutrophils in response to a stimulus requires that the neutrophils be exposed to a sufficient concentration of an LX-B analog. In accordance with the present invention, the attenuation of neutrophil activation can result in complete inhibition of certain aspects of neutrophil activation or, alternatively, markedly reduced activation. In accordance with the present invention, the inhibition of neutrophil activation can be measured by reference to a number of end points. These include the aggregation of neutrophils, the generation of superoxide anions by neutrophils, and the formation of certain pro-inflammatory leukotrienes through the 5-lypoxygenase pathway. The method in accordance with the present invention results in the attenuation of each of these aspects of neutrophil activation.

By virtue of the effect of the LX-B analogs on neutrophils, these substances are useful for preventing or treating inflammation, inflammatory responses, or inflammatory diseases and conditions. Accordingly, this method of the present invention permits treatment of a wide variety of diseases which are characterized by inflammation mediated in whole or in part through the activation of neutrophils. Such diseases and conditions include various forms of arthritis and asthma. Also included within the present invention are those inflammatory responses to physical injury, whether through physical trauma, radiation exposure, or otherwise.

The present invention relates not only to the treatment of existing inflammatory diseases or conditions, but also to the prevention of inflammation or inflammatory response in a mammal susceptible to the development of such a condition. Such mammals include, particularly, those with asthmatic conditions who risk exposure to the antigen or antigens which precipitate an acute asthmatic attack.

Whether the method of preventing or treating inflammation in accordance with the present invention is prophylactic or therapeutic, administration of an effective amount of the LX-B analog is required. The effective amount for administration is ordinarily that amount which is required to assure that the mammalian neutrophils involved in the inflammatory process will be exposed to a sufficient concentration of drug to inhibit their activation. Accordingly, a conventional therapeutic regimen for the administration of anti-inflammatory drugs is employed. Such a dosage regimen could consist of a single daily dosage, but would preferably employ multiple divided dosages per day. A dosage regimen can be effectively determined for each patient or animal by initial intravenous infusion at a low dosage level, e.g., 0.01 $\mu g/kg/min$ and thereafter increasing the dosage until the desired effect is obtained. Thereafter, oral dosages can be determined which will yield equivalent blood levels of drug.

The methods and compositions of the present invention are preferably designed and intended to treat humans, although are similarly useful in the treatment of veterinary animals.

The charts herein describe methods whereby the novel LX-B analogs are prepared. With respect to these charts, $R_{11}$ is an ester residue which can be either $C_1$–$C_{12}$ alkyl, $C_3$–$C_{10}$ cycloalkyl, $C_7$–$C_{12}$ arylalkyl, or optionally substituted phenyl. Appropriate ester residues of those described in U.S. Pat. No. 4,112,224.

$R_2$ represents an acyl protective group readily hydrolyzable under basic conditions. Such protective groups are known in the art and particularly include the benzoyl protective group. See U.S. Pat. No. 4,112,224 for a description of the protective groups useful in accordance with the present invention.

$R_3$ represents a readily hydrolyzable silyl protective group. Particularly, $R_3$ encompasses the use of t-butyldimethylsilyl as a protective group. Such protective groups are readily hydrolyzable under mild conditions, e.g., the use of tetra-n-butylamoniumfluoride.

$R_1$ represents an ester residue according to $R_{11}$, hydrogen, or a pharmacologically acceptable cation. Appropriate pharmacologically acceptable cations are those known to be useful with other eicosanoids and particularly include those described in U.S. Pat. No. 4,112,224.

X is cis—CH=CH— or trans—CH=CH— or —C≡C—.

With respect to the charts herein, Chart A describes a method by which the $C_1$–$C_7$ precursors of 20 carbon atom LX-B compounds are prepared while Chart B describes a method whereby the chemical intermediate providing the $C_8$–$C_{20}$ atoms for LX-B compounds are prepared. Thereafter, Chart C provides a method whereby these reaction products of Charts A and B respectively are fused to provide a 20 carbon atom intermediate for the preparation of LX-B, which is thereby converted to LX-B by the procedure of Chart D.

With respect to Chart A, the formula XXXI compound is known in the art or prepared by methods known in the art. For example, the formula XXXI compound is readily prepared from d-mannitol. Thereafter, the formula XXXI compound is transformed to the formula XXXII by a Wittig ω-carboxyalkylation. Accordingly, treatment of formula XXXI compound with 4-carboxybutyltriphenylphosphonium bromine yields the formula XXXII intermediate. Thereafter, the formula XXXIII iodolactone is prepared from the formula XXXII compound by conventional iodolactonization methods known for the synthesis of prostaglandins. The formula XXXIII compound is prepared as an isomeric mixture of iodolactones which are readily separable by ordinary means for preparing diasteromers, i.e., chromatographic separation.

Following resolution of the formula XXXIII compound into one of its two diasteromeric forms, the selected formula XXXIII diasteromer is then transformed to the formula XXXIV compound by deiodinization. Conventional reagents such as tri-n-butyltin hydride is employed. One of the two formula XXXIV products is prepared stereoselectively by this deiodinization depending upon the formula XXXIII epimer utilized as a reactant.

The formula XXXV hydroxy ester is then prepared from the formula XXXIV compound by reaction with an alcohol corresponding to the $R_{11}$ ester to be prepared in an amine base, e.g., triethylamine. A protective group is then introduced at the latent C-5 position by conventional means to yield the formula XXXVI intermediate.

The formula XXXVI compound is then hydrolyzed by treatment with acid to yield the corresponding formula XXXVII diol. For example, 80% aqueous acetic acid is employed in accomplishing this hydrolysis.

Thereafter, the formula XXXVIII aldehyde is prepared from a formula XXXVII diol by oxidation with an appropriate reagent. For this purpose lead tetraacetate is employed. Accordingly, the formula XXXVIII thusly produced is obtained in one of the two stereoisomeric forms depending upon the formula XXXIII isomer employed in the synthesis of the formula XXXVIII compound.

Chart B then describes the preparation of the formula XLVII acetylene from the formula XLI compound. The formula XLI compound is known in the art or prepared by methods known in the art. For example, the formula XLI compound can be prepared by hydrolysis of the corresponding ω-protected alcohol. The formula XLI compound thusly prepared is then oxidized to yield the formula XLII compound and thereafter transformed to the formula XLIII compound by treatment with the lithium salt of 1-methoxybut-1-en-3-yne. The formula XLIII compound thusly prepared is then reduced with sodium bis(2-methoxyethoxy)-aluminum hydride to yield the formula XLIV diene. This formula XLIV compound is then transformed to a corresponding mesylate by treatment with methanesulfonyl chloride in triethylamine followed by hydrolysis under basic conditions, e.g., aqueous potassium bicarbonate, to yield the formula XLV aldehyde. Wittig chloromethylation of this aldehyde, i.e., treatment with chloromethyltriphenylphosphonium chloride yields the corresponding formula XLVI isomers. Treatment of the formula XLVI isomeric mixture with lithium diisopropylamide yields the formula XLVII compound.

Chart C then describes the coupling reaction whereby the formula LI compound prepared according to Chart B and the formula LII compound (the latent C-5 beta isomer) prepared according to Chart A are joined. In this coupling reaction the lithium salt of the formula LI compound, prepared by known methods, is treated at low temperature with the formula LII compound to yield the formula LIII isomeric mixture (C-7). The formula LIII compound is then dehydroxylated, e.g., utilizing a Burgess salt at elevated temperature, to yield the isomeric mixture of formula LIV and formula LV compounds. The formula LIV compound can thereafter be converted to the formula LV compound by treatment with iodine.

Chart D provides a method whereby the formula LXI compound prepared according to Chart C can be converted to LX-B. The reaction sequence of Chart D provides that the formula LXII compound is prepared from the formula LXI compound by removal of the acyl protective group. This protective group is removed by conventional means, e.g., treatment with potassium carbonate in methanol. Thereafter, the remaining protective groups are hydrolyzed converting the formula LXII compound to the formula LXIII compound. As indicated above, these silyl groups are efficiently removed by treatment with tetra-n-butylamonium fluoride. Thereafter, selective hydrogenation converts the formula LXIII compound to the formula LXIV compound wherein X is cis—CH=CH—. This hydrogenation proceeds utilizing Lindlar catalyst or other conventional catalytic hydrogenation techniques. Finally, the formula LXIV ester is converted to the corresponding formula LXV acids and salts by conventional means for hydrolysis and salt formation.

In accordance with Chart D, the hydrogenation of the formula LXIII compound to the formula LXIV compound is optional. When hydrogenation is not undertaken, the corresponding formula LXV 8,9-didehydro-LX-B analogs are prepared, e.g., the compounds of formula XI. Similarly, the reaction steps of Charts C and D can be undertaken utilizing the latent C-5 isomer of the formula LII compound (as prepared in Chart A), to yield corresponding formula XII 5-epi and 5-epi-8,9-didehydro-LX-B compounds of formula XII.

Each of the LX-B compounds referred to above can also be prepared in the 6-iso configuration by employing the formula LIV 6-iso intermediate of Chart C in place of the formula LV compound. Accordingly, there are prepared the formula XVI 6-iso LX-B compounds.

By yet another modification of the procedure of Chart C, the formula LIII 7-hydroxy compound (or its C-5 isomer) may be employed in place of the formula LIII compound in the further procedure of Chart D. By this technique, corresponding formula XIV C-7 isomers are prepared.

These various alternate transformations described above are genericly described in Chart E. The formula LXXI compound of Chart E is derived from the formula XXXIII, formula XXXIV, or formula XXXV compound of Chart C or the C-5 isomers thereof. The C-5 isomers are prepared according to Chart C when the formula LII C-5 isomer is substituted for the formula LII compound depicted in Chart C. This formula LXXI compound is then subjected to deprotection and optional hydrogenation yielding the formula LXXII compound, the carboxyl group of which is optionally refunctionalized to yield a formula LXXIII product.

DESCRIPTION OF THE PREFERRED EMBODIMENTS

The present invention is more completely understood by the operation of the following examples.

EXAMPLE 1

7-oxo-5$\beta$-hydroxy-heptanoic acid, methyl ester, benzoate (Formula XXXVIII: $R_{11}$ is methyl and $R_2$ is benzoyl) and its 5$\alpha$ isomer.

Refer to Chart A.

A. A suspension of 4-carboxybutyltriphenyl phosphonium bromide (16.5 g) in 60 ml of tetrahydrofuran is treated at ambient temperature under nitrogen with a solution of sodium bis(trimethylsilyl)amide (13.6 g) in 50 ml of tetrahydrofuran. The resulting orange mixture is stirred at ambient temperature for 30 min., cooled to −78° C. and treated with the dropwise addition of formula XXXI, D-glyceraldehyde (4.4 g). Upon addition, the cold bath is allowed to slowly warm to ambient temperature and the reaction is stirred overnight. The mixture is quenched with water (100 ml) and the organic layers are concentrated under reduced pressure. Diethylether is added and the organic layer is extracted twice with water. The combined aqueous layers are acidified to pH 5 with 10% aqueous hydrochloric acid and extracted four times with ethyl acetate. The combined organic layers are dried over sodium sulfate, filtered and evaporated to give 8.30 g of crude formula XXXII isomers. ($^1$H NMR indicates an 8:1 mixture of cis/trans olefins.) The crude formula XXXII product is chromatographed on 350 g silica gel eluting with 5% methanol in methylene chloride to afford 5.50 g (76%) of the pure formula XXXII acid.

B. The reaction product of part A is dissolved in 52 ml of tetrahydrofuran and potassium bicarbonate (5.8 g) in 26 ml of water is added. The resulting mixture is stirred for 10 min. at ambient temperature, cooled to 0° C. and treated with potassium iodide (6.16 g) followed by iodine (19.5 g) in portions over a 5 min. period. The reaction is stirred in the dark at 0° C. for 30 min. and at ambient temperature overnight. The mixture is quenched with saturated sodium thiosulfate until clear, diluted with saturated sodium bicarbonate and extracted four times with ethyl acetate. The combined organic extracts are dried over sodium sulfate, filtered and evaporated to afford 7.79 g of crude formula XXXIII lactone. The crude product is chromatographed on 350 g of silica gel, eluting with 45% ethyl acetate/hexanes to afford 1.82 g of the formula XXXIII β-iodo isomer, 0.55 g of a mixture of isomers, and 4.32 g of the α-iodo isomer. Purified 6α-iodo isomer is recrystallized from hexane to give 3.14 g of a white crystalline solid of the following analytic characteristics:

(NMR, CDCl$_3$): δ1.36, 1.49, 1.80–2.11, 2.37–2.63, 3.73–4.33.

Infrared (CHCl$_3$): 2985, 2926, 2890, 1723, 1372, 1240, 1231, 1222, 1101, 1068, 1061, 848.

M.P.: 86.5°–93.0° C.

TLC (silica gel 60, F-254): R$_f$=0.20 in 50% ethyl acetate in isomeric hexanes.

($^{13}$NMR, CDCl$_3$): δ 18.4, 25.7, 26.5, 27.2, 29.4, 37.1, 68.6, 75.5, 79.9, 110.0, 170.1.

For the β-iodo isomer:
(NMR, CDCl$_3$): δ 1.34, 1.42, 1.88–2.02, 2.39–2.73, 3.88, 3.96, 4.10, 4.24, 4.60.

TLC (silica Gel 60, F-254): R$_f$=0.28 in 50% ethyl acetate in isomeric hexanes.

($^{13}$CNMR, COCl$_3$): δ 18.2, 25.7, 27.2, 29.3, 29.7, 40.8, 70.8, 75.9, 77.0, 110.9, 170.0.

C. The iodolactone (α-iodo isomer, part B, 1.241 g) is dissolved in 15 ml of toluene under nitrogen. The solution is treated with tri-n-butyltin hydride (1.18 ml) and 2,2'-azobis-2-methylpropronitrile (60 mg) and heated to 55° C. for 2 hr. The mixture is allowed to cool and is portioned between acetonitrile and hexane. The acetonitrile layer is washed three times with hexane. The combined hexane layers are extracted once with acetonitrile and the new acetonitrile layer is washed four times with hexane. The combined acetonitrile layers are evaporated and the residue is flash chromatographed on 65 g of silica gel, eluting with 60% ethyl acetate/hexanes to afford 0.749 g (96%) of the formula XXXIV lactone (5α-isomer). Characteristic analysis is:

NMR (CDCl$_3$): δ 1.36, 1.43, 1.50–2.15, 2.40–2.67, 3.62, 4.01–4.63.

TLC (silica gel 60, F-254): R$_f$=0.19 in 60% ethyl acetate in isomeric hexanes.

D. The iodolactone (5β-iodoisomer; 140 mg) is dissolved in 1 ml of toluene. The solution is treated with tri-n-butyl tin hydride (134 μl) and 2,2'-azobis-2-methylpropionitrile (6 mg). The mixture is heated at 50°–55° C. for 2 hr. The mixture is allowed to cool, taken up in acetonitrile, and washed four times with hexane. The acetonitrile layer is evaporated and the residue is chromatographed on silica gel (6 g) eluting with 60% ethyl acetate/hexanes, to give 62 mg (70%) of the formula XXXIV lactone (5β isomer). Characteristic analysis is:

NMR (CDCl$_3$): δ 1.37, 1.42, 1.73–2.13, 2.42–2.70, 3.55, 4.05–4.75.

TLC (silica gel 60, F-254): R$_f$=0.16 in 50% ethyl acetate in isomeric hexanes.

E. The lactone of part C (0.749 g) is dissolved in 26 ml methanol and 3 ml of triethylamine is added. The mixture is stirred at ambient temperature for 2 hr and 45 min. The organic layers are removed in vacuo to afford the formula XXXV hydroxy ester. The formula XXXV residue is dissolved in 9 ml of methylene chloride. Pyridine (3 ml) is added, followed by benzoyl chloride dropwise (0.61 ml). The mixture is stirred at ambient temperature for 2 hr, diluted with methylene chloride and washed twice with 5% hydrochloric acid, once with saturated sodium bicarbonate and once with brine. The organic layers are dried over sodium sulfate, filtered and evaporated. The residue is flash chromatographed on 65 g of silica gel, eluting with 20% ethyl acetate/hexanes to afford 1.17 g of the formula XXXVI benzoate methyl ester. Characteristic analysis is: NMR (CDCl$_3$): δ 1.30, 1.42, 1.67–2.17, 2.25–2.47, 3.57, 3.65, 3.95–4.37, 5.28, 7.47–7.70, 8.03–8.23.

Infrared (CHCl$_3$): 2986, 2953, 1740, 1716, 1451, 1370, 1275, 1256, 1214, 1175, 1114, 1070, 1026, 714.

TLC (silica gel 60, F-254): R$_f$=0.53 in 75% ethyl acetate in isomeric hexanes.

F. The formula XXXVI acetonide (part E, 88 mg) is dissolved in 3 ml of 80% aqueous acetic acid. The solution is stirred at room temperature for 7 hr. The mixture is carefully poured into saturated sodium bicarbonate and extracted four times with methylene chloride. The combined organics are dried over sodium sulfate, filtered and evaporated to afford 161 mg (97%) of the formula XXXVII diol.

Characteristic analysis is:
NMR (CDCl$_3$): δ 1.57–2.03, 2.23–2.57, 3.27–4.00, 3.68, 5.32, 7.40–7.67, 8.03–8.23.

TLC (silica gel 60, F-254): R$_f$=0.07 in 60% ethyl acetate in isomeric hexanes.

The formula XXXVII diol (part F, 91 mg) is dissolved in 4.5 ml of methylene chloride under nitrogen. The resulting solution is cooled to 0° C. and solid sodium bicarbonate (243 mg) is added followed by lead tetraacetate (221 mg) in portions. The mixture is stirred at 0° C. for 20 min, poured into water and extracted three times with methylene chloride. The combined organic layers are washed twice with saturated sodium bicarbonate, dried over sodium sulfate, filtered, and evaporated. The residue is taken up in ethyl acetate, filtered through a small plug of silica gel and concentrated to afford 81 mg of the title aldehyde (5β isomer). Characteristic analysis is:

NMR (CDCl$_3$): δ 1.63–1.87, 2.27–2.50, 2.73–2.90, 3.68, 5.62, 7.37–7.67, 8.03–8.17, 9.94.

TLC (silica gel 60, F-254): R$_f$=0.46 in 60% ethyl acette in isomeric hexanes.

H. Following the procedure of parts E, F, and G, but employing the 5β-isomer of part D in place of the 5α-isomer of part C, the corresponding formula XXXVIII 5α-isomer is obtained.

EXAMPLE 2

7α,8β-dihydroxy-propadeca-trans,trans-3,5-dien-1-yne bis(t-butyl-dimethylsilyl)ether (formula XLVII: R$_3$ is t-butyldimethylsilyl).

A. The 1-benzoyloxy-2α,3β-(t-butyldimethylsilyloxy)-octane is dissolved in 100 ml of methylene chloride under nitrogen. The solution is cooled to −78° C. and a solution of diisobutylaluminum hydride (13.15 ml, 1M) in methylene chloride is added dropwise via a syringe drive over a 45 min. period. The resulting mixture is stirred an additional 30 min. at −78° C. The reaction is quenched by the careful addition of 5 ml of methanol at −78° C. The mixture is allowed to warm to room temperature and 80 ml of 0.5M aqueous potassium tartrate was added. The 2-phase mixture is stirred vigorously for 90 min. The aqueous layer is extracted twice with methylene chloride and the combined organic layers are dried over sodium sulfate, filtered and evaporated. The crude formula XLI compound is chromatographed on 70 g of silica gel eluting with 5% ethyl acetate/hexanes to afford 2.35 g (96%) of the pure formula XLI alcohol.

B. A dry 100 ml 3-neck flask is charged with 14 ml of methylene chloride and 1.44 ml of pyridine under nitrogen. Solid chromium trioxide (0.89 g) is added in portions and the mixture is stirred at room temperature for 15 min. The part A alcohol (496 mg) in 2X 1 ml of methylene chloride is added via cannula (nitrogen pressure) all at once. The mixture is stirred for 90 min. at room temperature, filtered through 2 in. of florisil and the florisil was washed well with diethylether. The organic layers are evaporated and the resulting brown oil is chromatographed on 25 g of silica gel eluting with 2% ethyl acetate/hexanes to afford 476 mg of the formula XLII aldehyde.

C. A dry 50 ml 3-neck flask under nitrogen is charged with 3.4 ml of tetrahydrofuran and 0.12 ml of 1-methoxybut-1-en-3-yne. The solution is cooled to −78° C. and a solution of n-butyl lithium (0.89 ml, 1.37 mmol, 1.55M) in hexane is added slowly dropwise over a 10 min period. The resulting mixture is allowed to stir at −78° C. for 1 hr. The aldehyde (465 mg, part B) in 3X 0.4 ml tetrahydrofuran is added rapidly at −78° C. via cannula (nitrogen pressure) and the solution is stirred at −78° C. for 1 hr. The reaction is quenched by the addition of 0.3 ml of saturated potassium bicarbonate and the mixture is allowed to warm to room temperature. The mixture is diluted with 2% triethylamine/diethyl ether and solid sodium sulfate is added with stirring. After several minutes the organic layers were decanted and the solids are washed several times with 2% triethylamine/diethyl ether. The combined organics are dried over sodium sulfate and evaporated to afford 557 mg of the formula XLIII acetylenic alcohol. Characteristic analysis is:

NMR (CDCl$_3$): δ 0.12, 0.92, 1.17–2.03, 3.33–4.00, 3.73, 4.43–4.69, 6.27.

TLC (silica gel 60, F-254): R$_f$=0.15 in 10% ethyl acetate in isomeric hexanes.

D. A dry 50 ml 2-neck flask under nitrogen is charged with 10 ml of toluene and 0.39 ml (3.4M) of a solution of sodium bis(2-methoxyethoxy)-aluminum hydride (Red-Al) in toluene. The solution is cooled to −78° C. and the acetylenic alcohol (part C) in 3 ml of toluene is added dropwise. The reaction is warmed to 0° C. and stirred for 5 hr. The resulting reaction mixture is quenched with 0.2 ml water at 0° C. and 10 ml of 0.5M sodium potassium tartrate is added. The resulting mixture is diluted with ethyl acetate and stirred at ambient temperature for 12 hr. The aqueous layer is extracted twice with ethyl acetate and the combined organic extracts are washed with brine, dried over sodium sulfate and evaporated to give formula XLIV product.

E. The formula XLIV alcohol (part D) is dissolved in 7.5 ml of methylene chloride under nitrogen. The solution is cooled to −40° C. and triethylamine (0.35 ml) is added followed by methanesulfonyl chloride (0.13 ml) dropwise. The mixture is stirred at −40° C. for 30 min, quenched with 2 ml of saturated potassium bicarbonate and allowed to warm slowly to ambient temperature over a 2.5 hr period. The resulting mixture is diluted with methylene chloride and washed once with brine. The aqueous layer is re-extracted twice with methylene chloride and the combined organics are dried over sodium sulfate and evaporated. The resulting formula XLV material is chromatographed on 17 g silica gel, eluting with 4% ethyl acetate/hexanes to afford 87 mg of the pure formula XLV dienealdehyde. Characteristic analysis is:

NMR (CDCl$_3$): δ 0.00, 0.80, 0.83, 1.10–1.62, 3.58, 4.05, 5.90–6.43, 9.57.

TLC (silica gel 60, F-254): R$_f$=0.38 in 10% ethyl acetate in isomeric hexanes.

F. A dry 25 ml 2-neck flask under nitrogen is charged with 215 mg of chloromethyltriphenylphosphonium chloride and 3 ml of tetrahydrofuran. The mixture is cooled to 0° C. and 0.36 ml of a solution of n-butyl lithium in hexane is added slowly dropwise. The mixture is stirred at 0° C. for 30 min. The formula XLV aldehyde (part E, 184 mg) in 1.5 ml of tetrahydrofuran is added rapidly via cannula (nitrogen pressure) and the reaction is stirred at 0° C. for 45 min. The mixture is quenched with saturated sodium chloride and extracted three times with ethyl acetate. The combined organic extracts are dried over sodium sulfate and evaporated. The crude formula XLVI product is chromatographed on 25 g silica gel, eluting with hexanes, to afford 187 mg of the pure formula XLVI chloroolefin.

Characteristic analysis is:

NMR (CDCl$_3$): δ 0.03, 0.87, 0.89, 1.07–1.67, 3.58, 4.02, 5.57–6.73.

TLC (silica gel 60, F-254): R$_f$=0.16 in isomeric hexanes.

G. A dry 25 ml 2-neck flask under nitrogen is charged with 2.5 ml tetrahydrofuran and 119 μl of diisopropylamine. The solution is cooled to 0° C. and 0.41 ml (1.55M) of a solution of n-butyl lithium in hexane is added dropwise. The mixture is stirred at 0° C. for 20 min. and the chloroolefin (101 mg of part F) in 0.9 ml of tetrahydrofuran is added dropwise. The mixture is stirred at 0° C. for 30 min., quenched with 0.3 ml water and poured into saturated sodium chloride. The mixture is extracted three times with ethyl acetate and the combined organic extracts are dried over sodium sulfate, filtered and evaporated. The resulting material is chromatographed on 8 g silica gel, eluting with hexane, to afford 81 mg of the title acetylene.

Characteristics analysis is:

NMR (CDCl$_3$): δ 0.00, 0.85, 1.07–1.67, 2.97, 3.55, 3.99, 5.53, 5.78, 6.18, 6.68.

TLC (silica gel 60, F-254): R$_f$=0.12 in isomeric hexanes.

EXAMPLE 3

8,9-didehydro-LX-B 5-benzoate, 14,15-bis(t-butyldimethylsilyl)ether, methyl ester (Formula LV: R$_{11}$ is methyl, R$_2$ is benzoyl, and R$_3$ is t-butyldimethylsilyl) and is 6-isomer (Formula LIV: R$_{11}$, R$_2$ and R$_3$ as defined above).

Refer to Chart C.

A. A dry 25 ml 2-neck flask under nitrogen is charged with the formula LI acetylene (107 mg, Example 2) in 2.5 ml of tetrahydrofuran. The solution is cooled to −78° C. and 158 ml (1.55M) of a solution of n-butyl lithium in hexane is added slowly dropwise. The mixture is stirred at −78° C. for 1 hr. The formula LII aldehyde (81 mg, Example 1, 5β-isomer) in 0.4 ml of tetrahydrofuran is added slowly dropwise and the reaction is stirred at −78° C. for 1 hr. The reaction is quenched at −78° C. with 0.5 ml water and allowed to warm to room temperature. The mixture is poured into saturated sodium chloride and extracted three times with ethyl acetate. The combined organic extracts are dried over sodium sulfate and evaporated. The resulting material is chromatographed on 11 g silica gel, eluting with 17% ethyl acetate/hexanes to yield 89 mg of the formula LIII product as a mixture of diastereomers at C-7.

Characteristic analysis is:

NMR (CDCl$_3$): δ 0.01; 0.88; 1.13–1.58; 1.62–1.93; 1.99–2.20; 2.20–2.47; 3.57; 3.63; 3.97; 4.60; 5.13–6.75; 7.37–7.70; 8.01–8.20.

TLC (silica gel 60, F-254): R$_f$=0.28, 0.30 in 30% ethyl acetate in isomeric hexanes.

B. The mixture of alcohols (15.6 mg, Part A) is dissolved in 0.75 ml of tetrahydrofuran under nitrogen. A solution of 15.7 mg of (carboxysulfamoyl)triethylammonium hydroxide, inner salt, methyl ester in 0.1 ml of tetrahydrofuran is added at ambient temperature and the resulting mixture is heated at 50° C. for 90 min. The reaction is allowed to cool, poured into saturated sodium bicarbonate and extracted three times with ethyl acetate. The combined organic extracts are dried over sodium sulfate and evaporated. The resulting material is chromatographed on 1.0 g silica gel, eluting with 5% ethyl acetate/hexanes, to afford 4.3 mg of 3:1 mixture of cis/trans olefins of formula LIV and LV. The olefin isomers are separated by chromatography.

Characteristic analysis is:

(A) Formula LIV isomer.

NMR (CDCl$_3$): δ 0.02; 0.85; 1.15–2.05; 2.38; 3.5; 3.97; 3.64; 5.69; 5.80; 5.81; 5.92; 5.95; 6.17; 6.58; 7.40; 7.53; 8.03.

TLC (silica gel 60, F-254): R$_f$=0.27 in 10% ethyl acetate in isomeric hexanes.

(B) Formula LV isomer.

NMR (CDCl$_3$): δ 0.00; 0.85; 1.15–2.00; 2.33; 3.52; 3.65; 3.94; 5.54; 5.63; 5.75; 5.93; 6.10; 6.13; 6.54; 7.40; 7.52; 8.03.

TLC (silica gel 60, F-254): R$_f$=0.24 in 10% ethyl acetate in isomeric hexanes.

FORMULAS

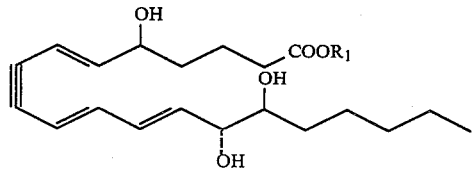

XI

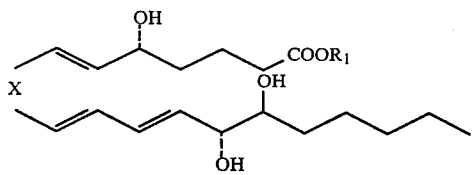

XII

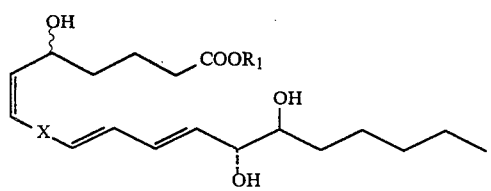

XIII

-continued
FORMULAS

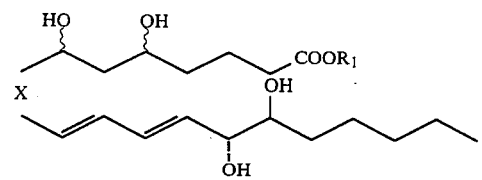

XIV

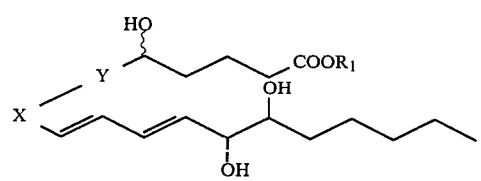

XV

CHART A

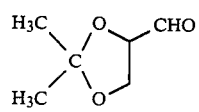

XXXI

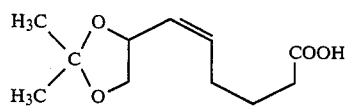

XXXII

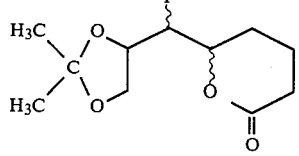

XXXIII

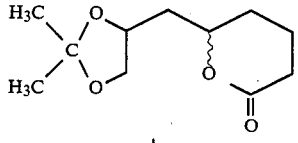

XXXIV

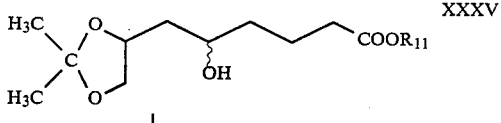

XXXV

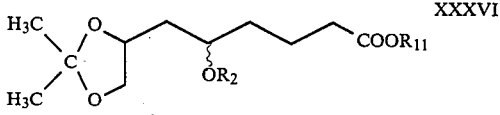

XXXVI

-continued
CHART A
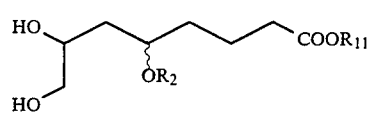 XXXVII
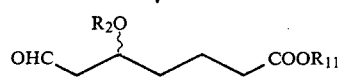 XXXVIII
CHART B
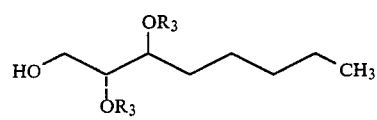 XLI
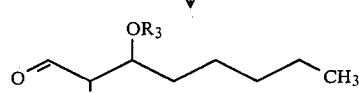 XLII
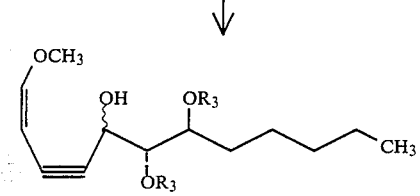 XLIII
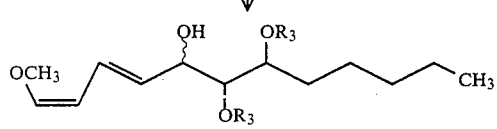 XLIV
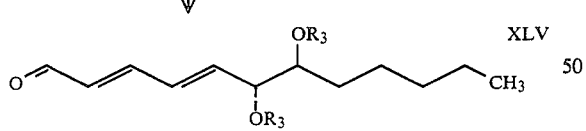 XLV
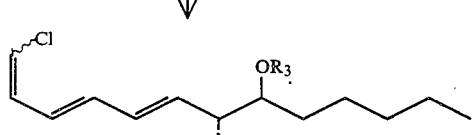 XLVI
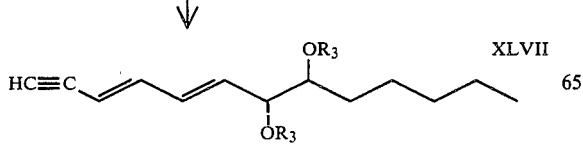 XLVII
CHART C
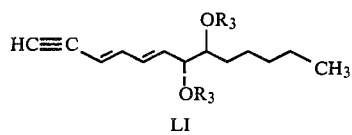 LI
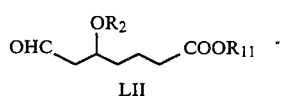 LII
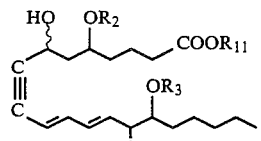 LIII
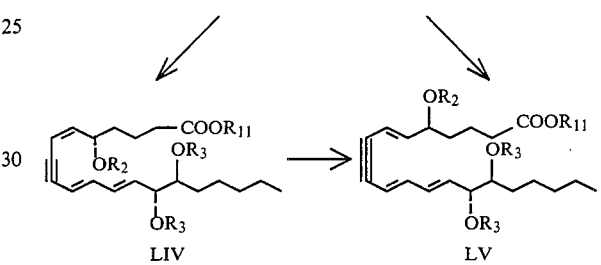
LIV    LV
CHART D
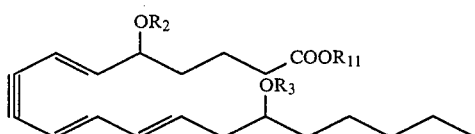 LXI
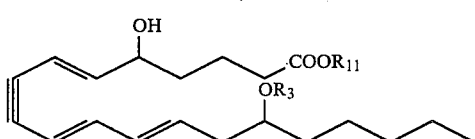 LXII
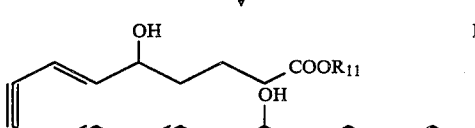 LXIII

CHART D

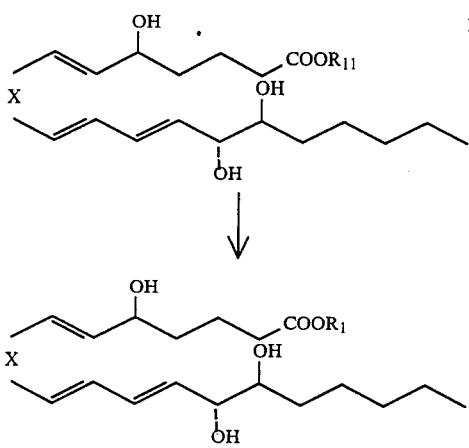

CHART E

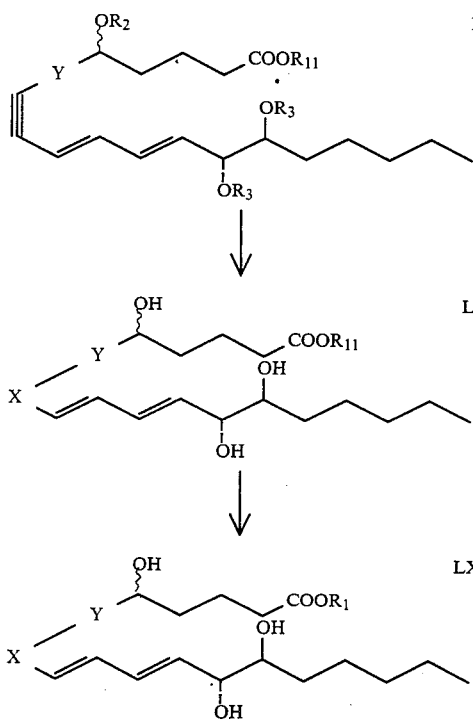

I claim:

1. An LX-B analog of formula XV

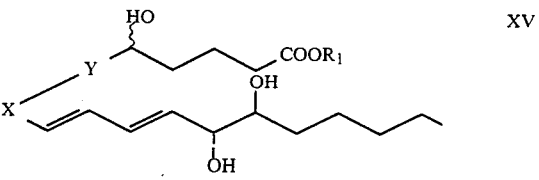

wherein X is cis—CH=CH— or —C≡C—;
wherein Y is cis—C=CH—, trans—CH=CH—, or —CH$_2$—CH(OH)—; and
wherein R$_1$ is hydrogen; C$_1$-C$_{12}$ alkyl; C$_3$-C$_{10}$ cycloalkyl; C$_7$-C$_{12}$ aralkyl; phenyl optionally substituted by one, two, or three C$_1$-C$_3$ alkyl, C$_1$-C$_3$ alkoxy, chloro, fluoro, or trifluoromethyl with the proviso that not more than two such substituents are other than alkyl; or a pharmacologically acceptable cation;
with the overall proviso that Y is trans—CH=CH— and X is cis—CH=CH— only when the hydroxyl configuration at C-5 is alpha.

2. 5-Epi-lipoxin B, a compound according to claim 1.
3. 8,9-Didehydro-lipoxin B, a compound according to claim 1.
4. 5-Epi-8,9-didehydro-lipoxin B, a compound according to claim 1.
5. 6-Iso-lipoxin B, a compound according to claim 1.
6. 5-Epi-6-iso-lipoxin B, a compound according to claim 1.
7. 8,9-Didehydro-6-iso-lipoxin B, a compound according to claim 1.
8. 5-Epi-8,9-didehydro-6,7-dihydro-7α-hydroxy-lipoxin B, a compound according to claim 1.
9. 6,7-Dihydro-7α-hydroxy-lipoxin B, a compound according to claim 1.
10. 5-Epi-6,7-dihydro-7α-hydroxy-lipoxin B, a compound according to claim 1.
11. 8,9-Didehydro-6,7-dihydro-7α-hydroxy-lipoxin B, a compound according to claim 1.
12. 5-Epi-8,9-didehydro-6,7-dihydro-7α-hydroxy-lipoxin B, a compound according to claim 1.
13. 6,7-Dihydro-7β-hydroxy-lipoxin B, a compound according to claim 1.
14. 5-Epi-6,7-dihydro-7β-hydroxy-lipoxin B, a compound according to claim 1.
15. 8,9-Didehydro-6,7-dihydro-7β-hydroxy-lipoxin B, a compound according to claim 1.
16. 5-Epi-8,9-didehydro-6,7-dihydro-7β-hydroxy-lipoxin B, a compound according to claim 1.
17. 5-Epi-lipoxin B, methyl ester, a compound according to claim 1.
18. 8,9-Didehydro-lipoxin B, methyl ester, a compound according to claim 1.
19. 5-Epi-8,9-didehydro-lipoxin B, methyl ester, a compound according to claim 1.
20. 5-Epi-lipoxin B, sodium salt, a compound according to claim 1.

* * * * *

UNITED STATES PATENT AND TRADEMARK OFFICE
CERTIFICATE OF CORRECTION

PATENT NO. : 4,576,758

DATED : March 18, 1986

INVENTOR(S) : Joel Morris

It is certified that error appears in the above-identified patent and that said Letters Patent is hereby corrected as shown below:

Column 18, line 11, "cis-C=CH-" should read -- cis-CH=CH- --.

Signed and Sealed this

Twenty-first Day of October, 1986

[SEAL]

Attest:

DONALD J. QUIGG

Attesting Officer

Commissioner of Patents and Trademarks